US012797134B2

(12) United States Patent
Temple et al.

(10) Patent No.: US 12,797,134 B2
(45) Date of Patent: Nov. 17, 2026

(54) ORIENTATION OF SURGICAL INSTRUMENTS AND IMPLANTS

(71) Applicant: DEPUY IRELAND UNLIMITED COMPANY, County Cork (IE)

(72) Inventors: Duncan Temple, Leeds (GB); David Wolfson, Leeds (GB)

(73) Assignee: DEPUY IRELAND UNLIMITED COMPANY, LOUGHBEG INDUSTRIAL ESTATE, Ringaskiddy (IE)

(*) Notice: Subject to any disclaimer, the term of this patent is extended or adjusted under 35 U.S.C. 154(b) by 732 days.

(21) Appl. No.: 18/041,619

(22) PCT Filed: Aug. 17, 2021

(86) PCT No.: PCT/EP2021/072842
§ 371 (c)(1),
(2) Date: Feb. 14, 2023

(87) PCT Pub. No.: WO2022/038141
PCT Pub. Date: Feb. 24, 2022

(65) Prior Publication Data

US 2023/0310088 A1 Oct. 5, 2023

(30) Foreign Application Priority Data

Aug. 17, 2020 (GB) ...................................... 2012817

(51) Int. Cl.
*A61B 34/20* (2016.01)
*A61F 2/38* (2006.01)
*A61F 2/46* (2006.01)

(52) U.S. Cl.
CPC .............. *A61B 34/20* (2016.02); *A61F 2/389* (2013.01); *A61F 2/4684* (2013.01); *A61B 2034/2048* (2016.02)

(58) Field of Classification Search
CPC . A61B 34/20; A61B 2034/2048; A61F 2/389; A61F 2/4684
See application file for complete search history.

(56) References Cited

U.S. PATENT DOCUMENTS 9,339,226 B2 * 5/2016 van der Walt ....... A61B 17/157
9,585,768 B2 * 3/2017 Sherman ............... A61F 2/4657
(Continued)

FOREIGN PATENT DOCUMENTS

WO WO-2004091419 A2 * 10/2004 ............. A61B 17/00
WO 2012084739 A1 6/2012
(Continued)

OTHER PUBLICATIONS

PCT Search Report From Corresponding PCT/EP2021/072842, Dated Nov. 24, 2021, 6 Pages.
(Continued)

*Primary Examiner* — Paula J Stice

(57) ABSTRACT

An apparatus and methods for guiding the orientation of an item of surgical equipment relative to a limb of a patient are described. A reference orientation sensor and a surgical equipment orientation sensor may be included. A data processing apparatus determines and stores an initial relative orientation between the reference orientation sensor and the surgical equipment orientation sensor from an initial reference orientation and an initial surgical equipment orientation, determines a current relative orientation between the reference orientation sensor and the surgical equipment sensor from a current reference orientation and a current surgical equipment orientation, and generates an output signal when the current relative orientation matches the reference relative orientation indicating that the surgical equipment orientation sensor currently has the same orien-
(Continued)

tation relative to the reference orientation sensor as when the initial relative orientation was determined.

13 Claims, 8 Drawing Sheets

(56) References Cited

U.S. PATENT DOCUMENTS

| | | | | |
|---|---|---|---|---|
| 11,207,085 | B2 * | 12/2021 | Thomas | A61B 17/157 |
| 2010/0250571 | A1 * | 9/2010 | Pierce | A61B 5/4528<br>600/587 |
| 2014/0276240 | A1 | 9/2014 | Stein | |
| 2014/0276858 | A1 | 9/2014 | Major | |
| 2014/0276871 | A1 | 9/2014 | Sherman | |
| 2017/0027590 | A1 | 2/2017 | Amiot | |
| 2022/0096248 | A1 * | 3/2022 | Dressler | A61F 2/4657 |

FOREIGN PATENT DOCUMENTS

| | | | |
|---|---|---|---|
| WO | 2012113054 | A1 | 8/2012 |
| WO | 2018075784 | A1 | 4/2018 |

OTHER PUBLICATIONS

GB Search Report From Corresponding GB Patent Application No. GB2012817.9, Dated Feb. 4, 2021, 4 Pages.

* cited by examiner

ORIENTATION OF SURGICAL INSTRUMENTS AND IMPLANTS

CROSS-REFERENCE TO RELATED APPLICATIONS

This application is a national stage entry under 35 U.S.C. § 371(b) of PCT International Application No. PCT/EP2021/072842, entitled "Orientation of Surgical Instruments and Implants" and filed Aug. 17, 2021, which claims priority to Great Britain Patent Application No. 2021817.9, filed on Aug. 17, 2020, the entire disclosures of both of which are expressly incorporated herein by reference.

The present disclosure relates to apparatus, systems and methods of use in surgery, and in particular to data processing apparatus, data processing systems, data processing methods and associated surgical apparatus and methods.

In many surgical procedures it may be desirable to be able to position and/or orient a piece of surgical equipment or implant relative to a part of a body of a patient. For example, during orthopaedic surgical procedures, it may be desirable to be able to position and/or orient an instrument or an implant relative to a bone of a patient. It may be the position, i.e. the location in space, and/or the orientation, i.e. the direction, of the instrument or implant which is important. Sometimes it may be the position and/or orientation relative to a native feature of the patient's anatomy and in other instances, it may be the position and/or orientation relative to a modified feature of the patient's anatomy, e.g. a resected part of the patient's bone, that is relevant.

A variety of ways of trying to position and/or orient surgical equipment are generally known. Some approaches involved the use of secondary instrumentation which may be attached to the patient's anatomy in order to provide a guide relative to which the surgical equipment may be positioned and/or oriented. However, the use of ancillary instrumentation may interfere with the surgical procedure and impeded access to the surgical site. Also, the accuracy of positioning and/or orienting that may be achieved may be relatively low.

More complicated approaches may also be used including various wired and wireless tracking systems which can use various forms of signals, e.g. acoustic, magnetic, electromagnetic, in order to track the position and/or orientation of items of surgical equipment within a reference frame or co-ordinate frame of the tracking system. However, although such systems may provide great accuracy and have other benefits, they may also be quite costly and not readily available. Further, there may be extra time and further surgical steps required in order to carry out surgical procedures using more sophisticated tracking systems and computer assisted surgery (CAS) systems.

For example, WO 2012/084739 describes a system using three wireless orientation/position sensors, a computer and a pair of glasses including a transparent screen to be worn by the surgeon while simultaneously viewing a patient. A first sensor is attached to the patient's pelvis and a second sensor is on the end of an instrument attached to a trial acetabular cup. The computer receives wireless signals from the first and second sensors and stores the position of the trial cup relative to the first sensor as a predetermined position value. A third sensor is on the end of an introducer for introducing an acetabular cup. The computer received wireless signals from the first and third sensors and stores the position of the cup relative to the first sensor as a comparison position value. The computer transmits visual signals of the predetermined position value and the comparison position value to the pair of glasses so that the visual signals can be displayed to the user using the transparent screen.

Therefore methods and apparatus permitting the orientation of surgical equipment relative to a body part to be accurately determined in a simple, easy to use and relatively unobtrusive manner would be beneficial.

A first aspect of the disclosure provides a surgical system. The surgical system may comprise a reference orientation sensor operable to determine a reference orientation and having a first attachment feature by which the reference orientation sensor is attachable to a limb of a patient in use. The surgical system may further comprise a surgical equipment orientation sensor operable to determine a surgical equipment orientation and having a second attachment feature by which the surgical equipment orientation sensor is attachable to an item of surgical equipment in use. The surgical system may further comprise a data processing apparatus, the data processing apparatus including a data processor and a storage device storing non-transitory instructions executable by the data processor to: determine and store an initial relative orientation between the reference orientation sensor and the surgical equipment orientation sensor from an initial reference orientation and an initial surgical equipment orientation; determine a current relative orientation between the reference orientation sensor and the surgical equipment sensor from a current reference orientation and a current surgical equipment orientation; and generate an output signal when the current relative orientation matches the reference relative orientation indicating that the surgical equipment orientation sensor currently has the same orientation relative to the reference orientation sensor as when the initial relative orientation was determined.

The surgical equipment orientation sensor may include an output device arranged to receive the output signal and to change state when the output signal is received.

The output device may be a visual output device. The visual output device may be one or more lights. The one or more lights may change colour when the output signal is received.

The output device may additionally or alternatively be an acoustic device. The acoustic device may start or stop emitting an acoustic signal, or change an acoustic signal, when the output signal is received.

The data processing apparatus may be included in the surgical equipment orientation sensor and/or the reference orientation sensor. A communication link may be provided between the surgical equipment orientation sensor and the reference orientation sensor. The communication link may be a wireless or a wired communication link. The reference orientation sensor may include one or more user interface or input/output elements or features by which a user may enter command signals and/or control signals to the reference orientation sensor.

The data processing apparatus may be a separate device to the surgical equipment orientation sensor and the reference orientation sensor. The reference orientation sensor may include a first communication interface via which the reference orientation sensor can transmit to the data processing apparatus. The surgical equipment orientation sensor may include a second communication interface via which the surgical equipment orientation sensor can communicate with the data processing apparatus. The communication interfaces may be wireless communications interfaces or wired communication interfaces.

The surgical system may further comprise a trial implant having a trial attachment feature to which the surgical equipment orientation sensor is releasably attachable and/or a prosthetic implant having a prosthetic attachment feature to which the surgical equipment orientation sensor is releasably attachable.

The trial attachment feature may be configured to provide a first orientation of the surgical equipment orientation sensor to the trial implant when attached to the trial implant by the trial attachment feature. The prosthetic attachment feature may be configured to provide a second orientation of the surgical equipment orientation sensor to the prosthetic implant when attached to the prosthetic implant by the prosthetic attachment feature. The first orientation and the second orientation may be the same.

The prosthetic implant may include an elongate member configured to be received in a cavity defined by a bone of a patient. The elongate member may include at least one formation configured to interact with bone to inhibit rotation of the elongate member relative to the bone. The elongate member may include at least one formation configured to provide press-fit fixation of the stem within bone.

The elongate member may be a stem. The or each formation may be a self-cutting tooth.

The second attachment feature may comprise a pair of mutually opposed sprung members arranged to interact with a feature of the item of surgical equipment and/or and centralise the surgical equipment orientation sensor relative to the feature of the item of surgical equipment.

The reference orientation sensor may include a support formation configured to interact with a bony anatomical feature of the limb of the patient and to resist movement of the reference orientation sensor relative to the limb of the patient. The support formation may comprise a plurality of members. The plurality of members may each comprise a foot. The plurality of members may be arranged to straddle the bony anatomical feature. The bony anatomical feature may be a ridge.

The item of surgical equipment may be an orthopaedic implant.

The orthopaedic implant may be a tibial implant. The tibial implant may be or include a tibial tray. The tibial implant may be a trial tibial implant or a prosthetic tibial implant.

The limb may be a tibia of the patient

The surgical system may further comprise a surgical instrument having an instrument attachment feature to which the surgical equipment orientation sensor is releasably attachable.

The surgical system may and further comprise a surgical instrument or an implant, the surgical instrument or implant having an attachment feature to which the surgical equipment orientation sensor is releasably attachable and also having a bone modifying feature configured to modify a bone in use. The bone modifying feature may be configured to cut a bone, to deform a bone or otherwise change or modify the shape or structure of the bone in use.

The reference orientation sensor may comprise a first inertial measurement unit. The surgical equipment orientation sensor may comprise a second inertial measurement unit.

A second aspect of the disclosure provides a data processing method for guiding the orientation of an item of surgical equipment, comprising: receiving initial reference orientation data from a reference orientation sensor and initial surgical equipment orientation data from a surgical equipment orientation sensor; determining an initial relative orientation between the reference orientation sensor and the surgical equipment orientation sensor from the initial reference orientation data and the initial surgical equipment orientation data; storing the initial relative orientation; receiving current reference orientation data from the reference orientation sensor and current surgical equipment orientation data from the surgical equipment orientation sensor and determining a current relative orientation between the reference orientation sensor and the surgical equipment sensor from the current reference orientation data and the current surgical equipment orientation data; and generating an output signal when the current relative orientation matches the reference relative orientation indicating that the surgical equipment orientation sensor currently has the same orientation relative to the reference orientation sensor as when the initial relative orientation was determined.

A third aspect of the disclosure provides a storage medium storing non-transitory instructions executable by a data processor to carry out the method of the second aspect of the disclosure.

A fourth aspect of the disclosure provides a data processing apparatus including: a data processor; and the storage medium of the third aspect of the disclosure, wherein the storage medium is in communication with the data processor.

A fifth aspect of the disclosure provides a method for guiding the orientation of an item of surgical equipment relative to a limb of a patient. The method may comprise one or more of: attaching a reference orientation sensor to a limb of a patient; modifying a part of the limb of the patient as part of a surgical procedure being carried out on the limb; engaging an item of surgical equipment with the part of the limb that has been modified; determining an initial reference orientation using the reference orientation sensor and determining an initial surgical equipment orientation using the surgical equipment orientation sensor attached to the item of surgical equipment; determining and storing an initial relative orientation between the reference orientation sensor and the surgical equipment orientation sensor from the initial reference orientation and the initial surgical equipment orientation; engaging a further item of surgical equipment with the part of the limb that has been modified; determining a current relative orientation between the reference orientation sensor and the surgical equipment sensor from a current reference orientation and a current surgical equipment orientation while the surgical equipment sensor is attached to the further item of surgical equipment; and generating an output signal when the current relative orientation matches the reference relative orientation indicating that the surgical equipment orientation sensor currently has the same orientation relative to the reference orientation sensor as when the initial relative orientation was determined.

The item of surgical equipment and/or the further item of surgical equipment may be a surgical instrument or an implant. The implant may be a trial implant or a prosthetic implant. The surgical instrument or the implant may include a bone modifying feature configured to change a bone of the patient. The surgical instrument of implant may include a feature to which the surgical equipment orientation sensor is releasably attachable.

The limb may be the upper leg of the patient. The limb may be the femur.

The limb may be the lower leg of the patient.

The item of surgical equipment may be a trial orthopaedic implant and the further item of surgical equipment may be a prosthetic orthopaedic implant.

The orthopaedic implant may be or include a tibial implant and in particular may be or include a tibial tray.

The prosthetic orthopaedic implant may include a stem providing press-fit fixation within a bone. The stem may be a self-cutting stem.

The method may further comprise: attaching a yet further item of surgical equipment using at least one fastener to the part of the limb that has been modified; and using the yet further item of surgical equipment to further modify the part of the limb that has been modified.

The method may further comprise securing the item of surgical equipment to the part of the limb that has been modified using the at least one fastener after further modifying the part of the limb.

The or each at least one fastener may be a bone pin. The yet further item of surgical equipment may be a guide. The guide may be a drill or cutting guide. The yet further item of surgical equipment may be used to form a pilot hole in a bone of the limb.

Modifying the part of the limb may include resecting a bone of the limb and/or forming a cavity in a bone of the limb.

The method may further comprise further modifying the part of the limb before engaging said further item of surgical equipment.

Embodiments of the disclosure will now be described, by way of example only, and with reference to the accompanying drawings, in which.

In the Figures of drawings, like items share common reference signs unless indicated otherwise.

Figure 1:
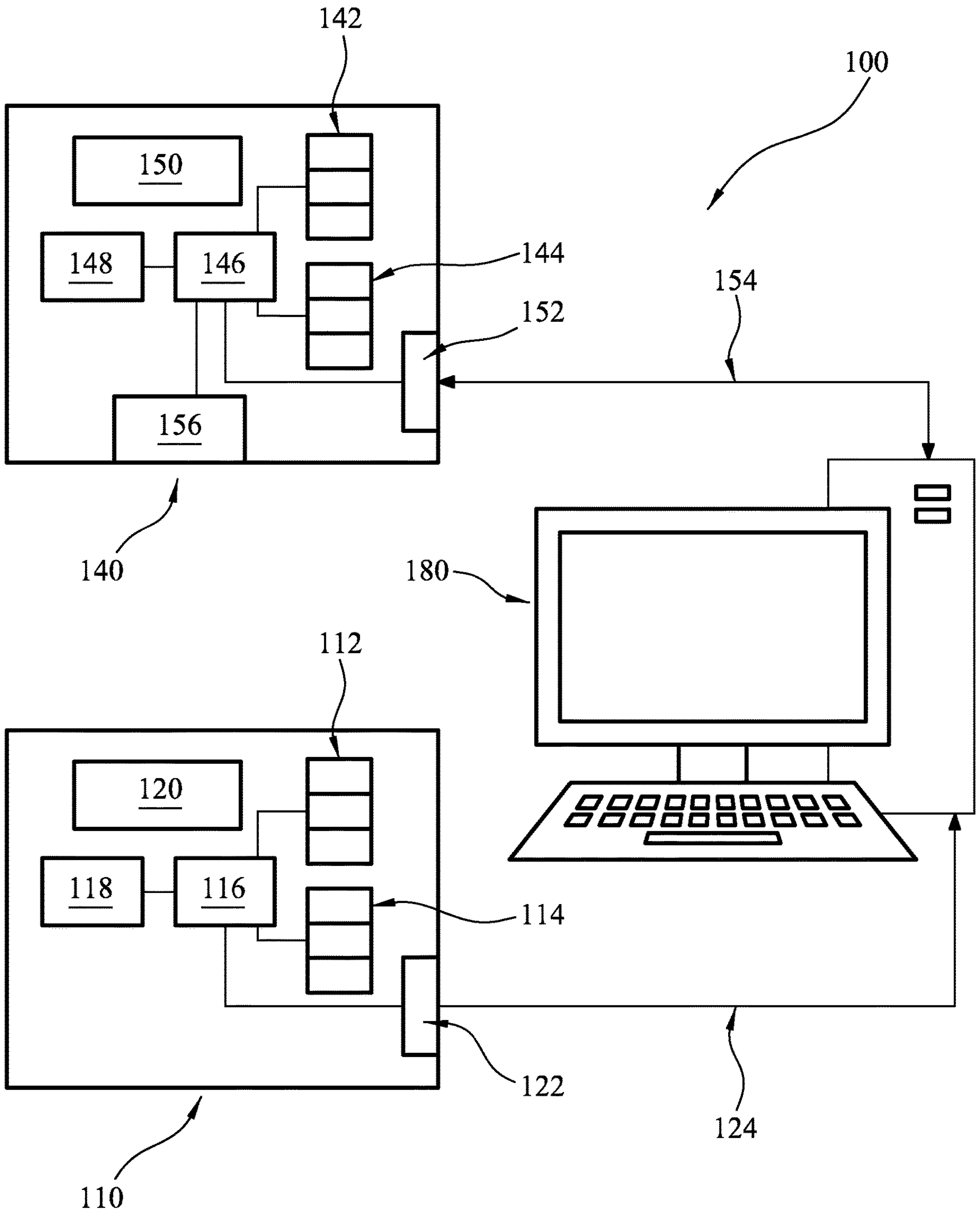
FIG. 1 shows a schematic block diagram of a first embodiment of a data processing system according to an aspect of the disclosure.

With reference to FIG. 1, there is shown a schematic block diagram of a first embodiment of a data processing system 100 according to an aspect of the disclosure. The data processing system 100 includes a first orientation sensor 110, a second orientation sensor 140 and a data processing device 180 in the form of a general purpose programmable computer.

The first orientation sensor 110 will generally be referred to herein as a reference orientation sensor. The orientation sensor 110 is operable to determine its orientation and output a signal including data items specifying its orientation. In one embodiment, the data items may be angles defining the pitch, yaw and roll of the orientation sensor 110 also referred to as Euler angles.

The reference orientation sensor 110 may include first to third accelerometers 112 and first to third gyroscopic sensors 114 in communication with a data processor 116. The data processor 116 may be in communication with a storage device or memory 118 providing local memory and also storing instructions for operating the reference orientation sensor 110. An on-board power supply, such as a battery 120, is also provided to supply electrical power to the various parts of the orientation sensor. A communications interface 122 is also provided via which detected angular information may be output. In some embodiments the communication interface 122 may be a wireless interface, for example using Bluetooth or Wi-Fi. Other embodiments, the communication interface 122 may be a wired interface and provide a wired communication link 124, for example using the USB protocol to transfer angular data to the computer 180. When a wired communication link is provided, then the wired communication link may also provide a source of power to the reference orientation sensor 110 in which case the on-board power supply 120 may be omitted. An on/off switch and other user interface elements may also be provided.

The second orientation sensor 140 is generally similar to the first orientation sensor 110. The second orientation sensor 140 will generally be referred herein as the surgical equipment or simply surgical orientation sensor as this is intended to be attached to various items of surgical equipment, such as surgical instruments and/or surgical implants, including trial implants and prosthetic implants.

The surgical equipment orientation sensor 140 similarly includes first to third accelerometer 142 and first to third gyroscopic sensors 144 connected to the data processor 146 which in turn is connected to a local storage device or memory 148. A local supply of electrical power 150, such as a battery, is also provided for powering the various electrical components. Also, a communication interface 152 is provided which provides a two-way communication link 154 to the computer 180. In some embodiments the communication link 154 and communication interface 152 may support a wireless communication, for example using Bluetooth or Wi-Fi. In other embodiments, a wired communication link 154 may be provided and the communication interface 152 may support the USB protocol. The surgical orientation sensor also includes an output device 156, which may be in the form of a light, such as an LED, which provides a visible signal to a user to indicate alignment, as described in greater detail below. Other user interface elements may also be provided, such as on/off power switch and a power light which is illuminated when the orientation sensor is powered on.

Similarly to the first orientation sensor 110, the second orientation sensor 140 outputs a signal indicating the current values for the detected angle of pitch, yaw and roll of the sensor as time series data.

A suitable device for the orientation measuring parts of the orientation sensors is a MovSens nine-degrees of freedom IMU.

The data processing device 180 may be in the form of a general purpose or a specific purpose computing device. The general purpose computing device may include statistical software to carry out data processing operations as described in greater detail below, particularly with reference to FIG. 9.

The data processing system illustrated in FIG. 1 may be provided as part of a larger surgical system including various surgical instruments and/or implants which can be used in order to carry out a surgical procedure to allow the orientation of a subsequently used item of surgical equipment to be matched to the orientation of a previously used item of surgical equipment, as also described in greater detail below.

Figure 2:
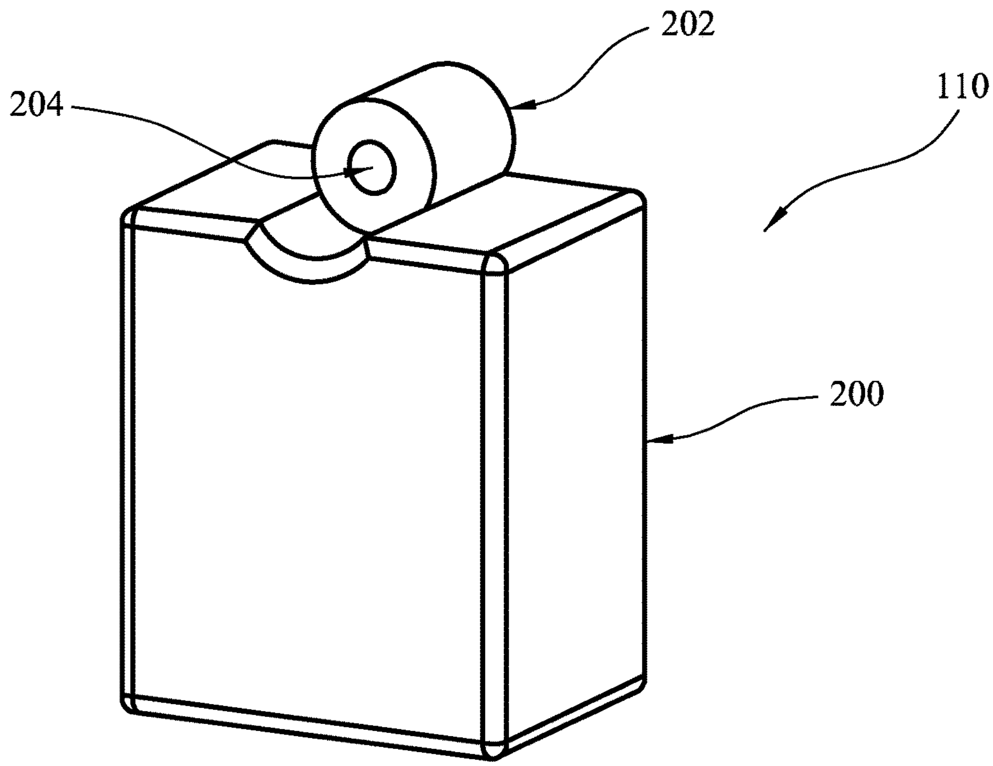
FIG. 2 shows a perspective view from the front of a reference sensor part of the system of FIG. 1.
Figure 3:
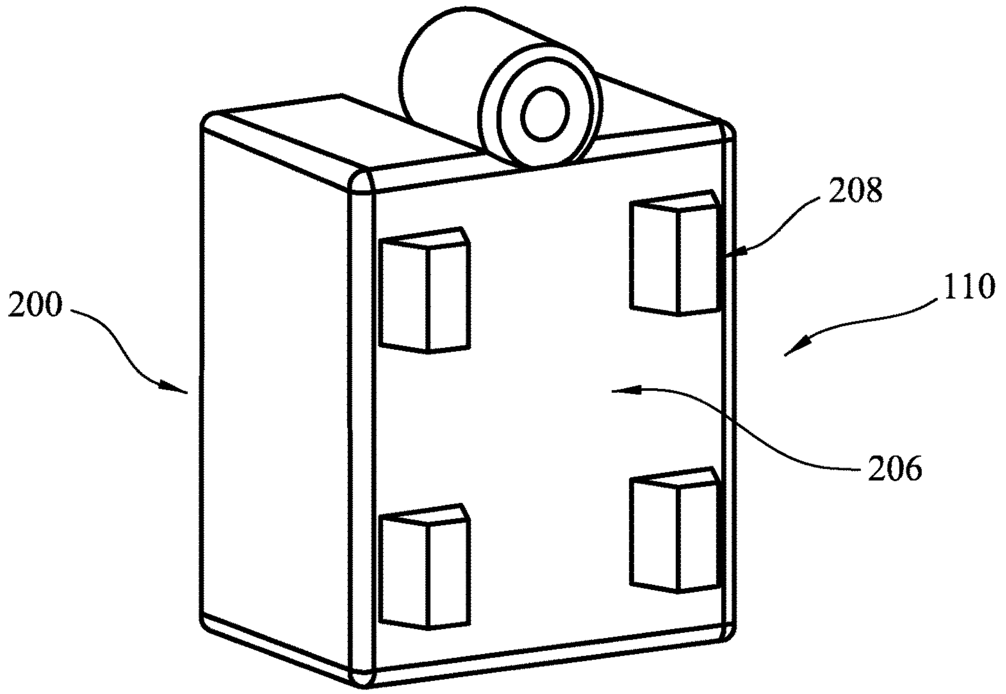
FIG. 3 shows a perspective view from the rear of the reference sensor shown in FIG. 2.

FIGS. 2 and 3 show perspective front and rear views of the reference orientation sensor 110. The reference orientation sensor 110 includes a housing 200 having a generally rectangular form. A top end of the housing 200 includes an attachment feature 202 having a generally annular form defining a bore 204 there through. Bore 204 is dimensioned and sized to accept a headed surgical pin to allow the reference orientation sensor 110 to be attached to a bone of the patient in use. In particular, the reference orientation sensor can be attached to the tibia of a patient. In other embodiments, a plurality of bores each for receiving a respective pin may be provided.

A rear face 206 includes four proud formations, e.g. formation 208, generally in the form of feet which are arranged to straddle the anterior tibial crest and help stabilise and minimise movement of the reference orientation sensor on the tibia and secured thereto by a single surgical pin. It will be appreciated that other mounting formations may also be provided depending on the anatomical feature of the bone to which the reference orientation sensor is to be attached.

The housing 200 may be formed of a biocompatible material, and in particular a plastic which can be sterilisable and to isolate the internal electronic components from the surgical environment. For example the housing may be made of polycarbonate and may be formed by injection molding.

Figure 4:
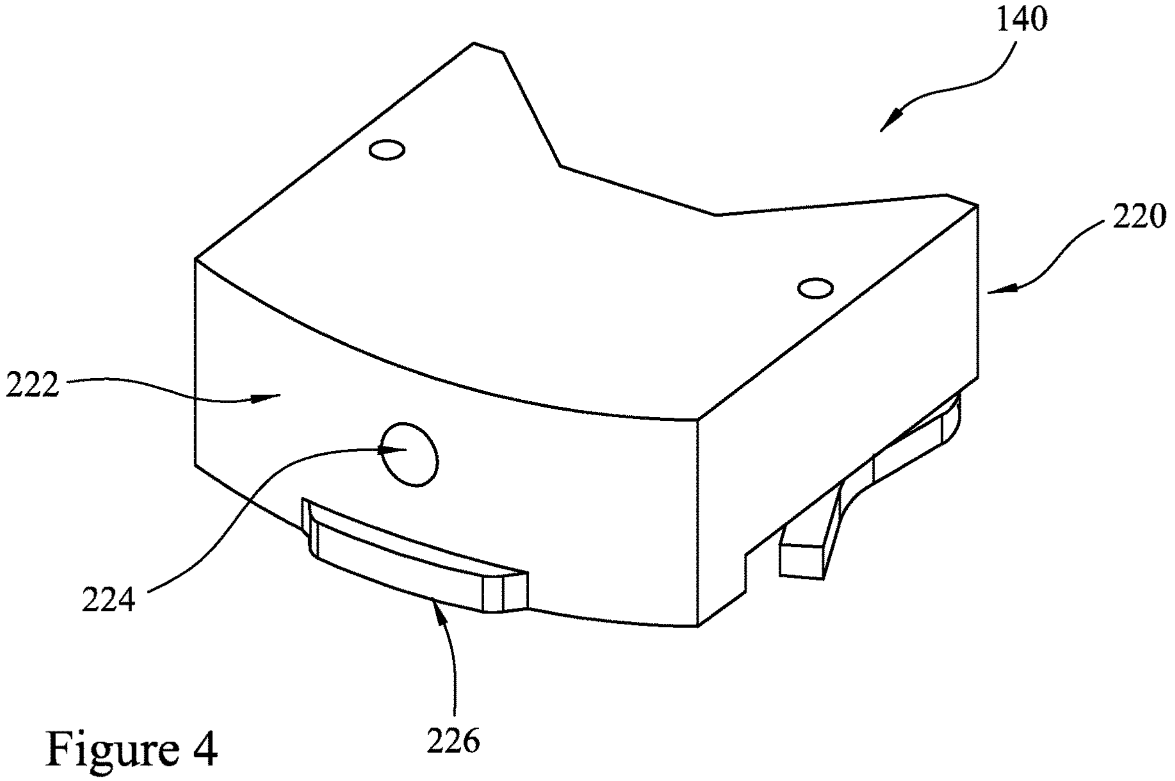
FIG. 4 shows a perspective view from above of a surgical sensor part of the system of FIG. 1.
Figure 5:
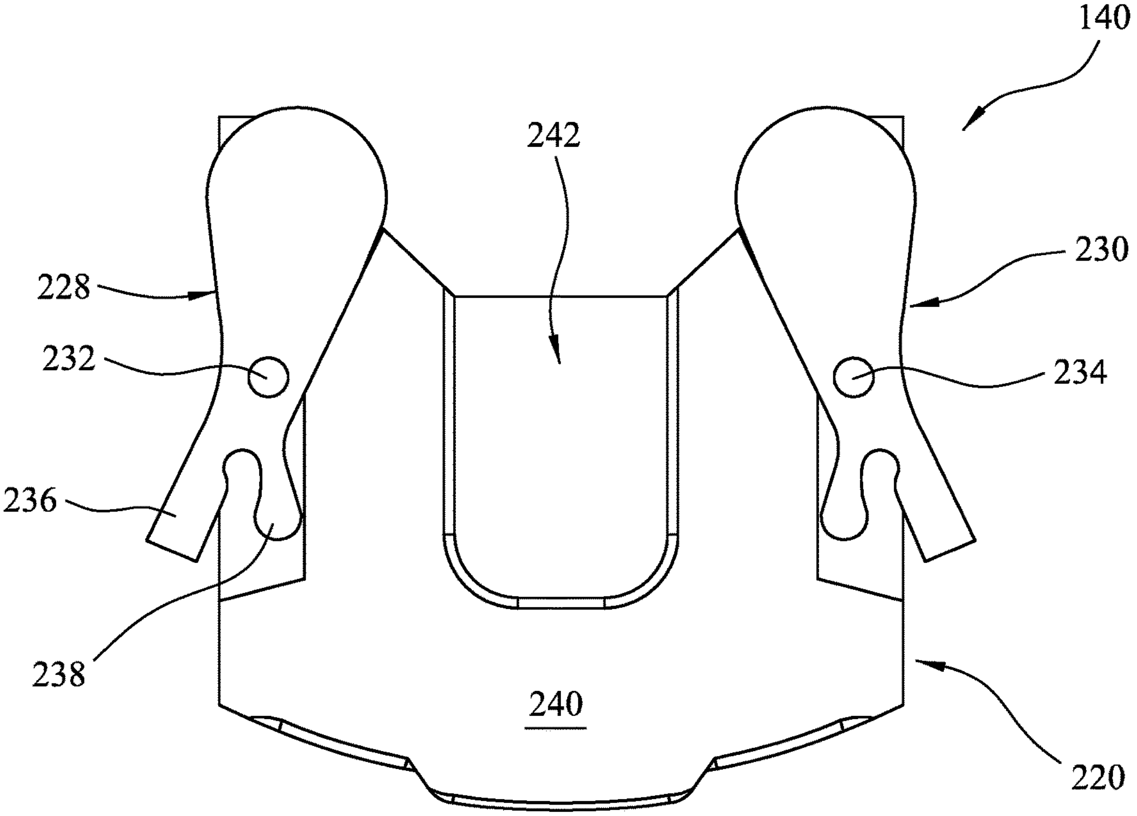
FIG. 5 shows an elevation from below of the surgical sensor shown in FIG. 4.

FIG. 4 shows a perspective view, generally from above, of the surgical orientation sensor 140 and FIG. 5 shows an elevation from below of the surgical orientation sensor 140. Similarly to the reference orientation sensor, the surgical orientation sensor 140 includes a housing 220 made of a plastic, such as polycarbonate, within which the electronic components are sealed so that the surgical orientation sensor is sterilisable for use. The housing 220 of the surgical orientation sensor 140 has an outer form configured and arranged to allow the housing to mate with corresponding features on the item of surgical equipment to which it is intended to be attached. In the embodiment described herein, the item of surgical equipment is a tibial tray implant. However, it will be appreciated that the housing 220 may have other forms depending on the item of surgical equipment to which it is to be attached in user.

A front face of the housing 222 defines an aperture via which an indicator light 224 is exposed to a user. A tab or lip formation 226 extends outwardly from the front face 222.

As best illustrated in FIG. 5, the surgical orientation sensor 140 also includes a clip mechanism in the form of a pair of sprung tabs 228, 230 mounted on respective shafts 232, 234. Each tab includes an outer limb, e.g. 236 and a resilient inner limb, e.g. 238 which biases the tab toward the centre of the housing.

The underside surface 240 of the housing 220 also defines a key way 242 for accepting a part of the tibial tray as described in greater detail below.

Figure 6:
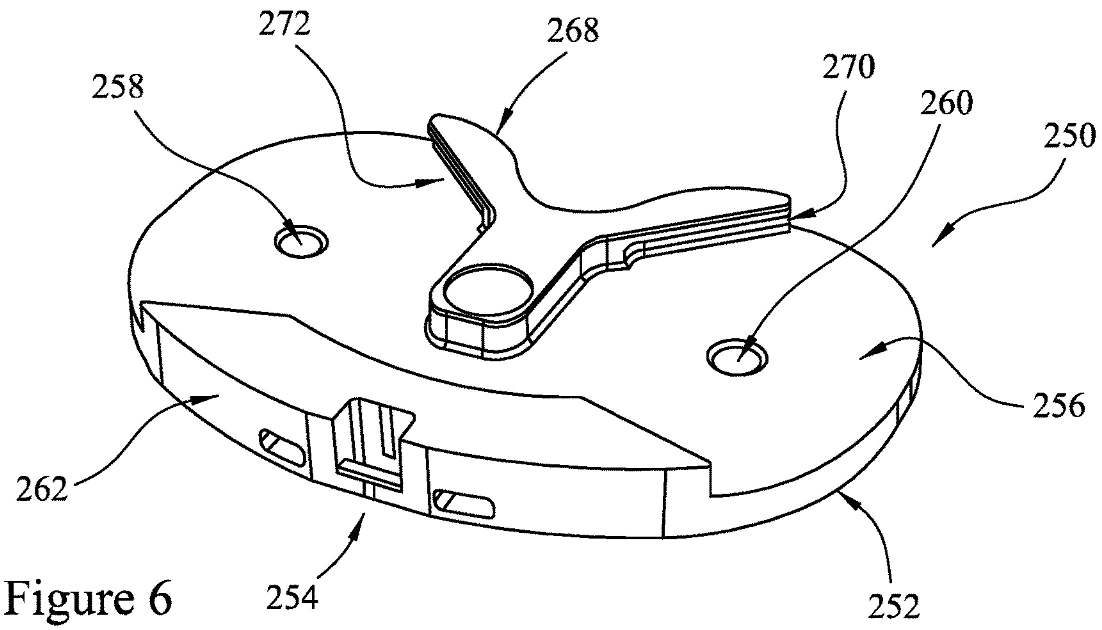
FIG. 6 shows a perspective view from above of a trial implant to which the surgical sensor is releasably attachable.

FIG. 6 shows a perspective view of a trial tibial implant 250. The trial tibial implant 250 has a generally curved plate-like construction and has a generally flat planar under surface 252. An anterior portion of the tibial trial implant 250 defines a plurality of female features for accepting an alignment handle which may be releasably attached to the trial to allow correct positioning of the trial along the resected tibial surface during trialling. An upper surface 256 of the main body of the tibial trial 250 has a generally flat planar form and is generally parallel to the flat planar under-surface 252. A first pinhole 258 and a second pinhole 260 are defined within the body of the tibial trial. The anterior part 262 also defines an undercut (not visible in FIG. 6) for receiving the tab 226 of the surgical orientation sensor 140.

The tibial trial may also include a stem trial extending generally perpendicularly from the under surface 252 of the tibial tray trial 250. The stem trail is generally similar to the prosthetic stem 320 illustrated in FIG. 7 below, but either without cutting teeth, so that it can be rotated within the bone, or the trial stem may rotatably attached to the tray trial. For example., the stem trial may be loosened from the trial with a bolt so that tray trial may be rotated about the axis of the stem trial, and then tightened up to lock the relative orientation of the tray and stem.

The prosthetic tibial implant, corresponding to the trial tibial implant 250, also includes an articulating member, often provided as a polymer, against which the condyles of the femoral implant component articulate in use. The articulating portion of the tibial implant is generally made from a different material to the main body of the tibial prosthetic implant and therefore the articulating portion is usually attached to the main body. Hence, the trial tibial implant 250 includes an attachment formation 268 having a generally similar form in a corresponding attachment formation of the corresponding prosthetic tibial implant. As illustrated in FIG. 6, the attachment formation 268 has a generally Y-shaped form and includes respective undercuts, e.g. 270, in respective arms of the attachment formation. The respective undercuts, 270, 272 are positioned and arranged to interact with the sprung tabs 228, 230 to allow the surgical orientation sensor 140 to be releasably attached to the tibial trial implant 250 by engaging tab 226 in the anterior portion and engaging inner edges of the tabs with the respective undercuts 270, 272 and then releasing the sprung tabs to secure the surgical orientation sensor to the tibial trial in use.

It will be appreciated that the under-surface of surgical orientation sensor is generally planar and hence abuts the upper surface 256 of the tibial trial implant 250 and hence the housing of the surgical orientation sensor is generally parallel to the plane of the under-surface 252 of the tibial trial. Hence, the surgical orientation sensor 140, once attached to the tibial trial 250 has a fixed orientational relationship thereto. It will be appreciated that in the illustrated embodiment the surgical orientation sensor housing is generally parallel to the under-surface 252 of the tibial trial. However, in other embodiments, other fixed orientation relationships may be used.

Figure 7:
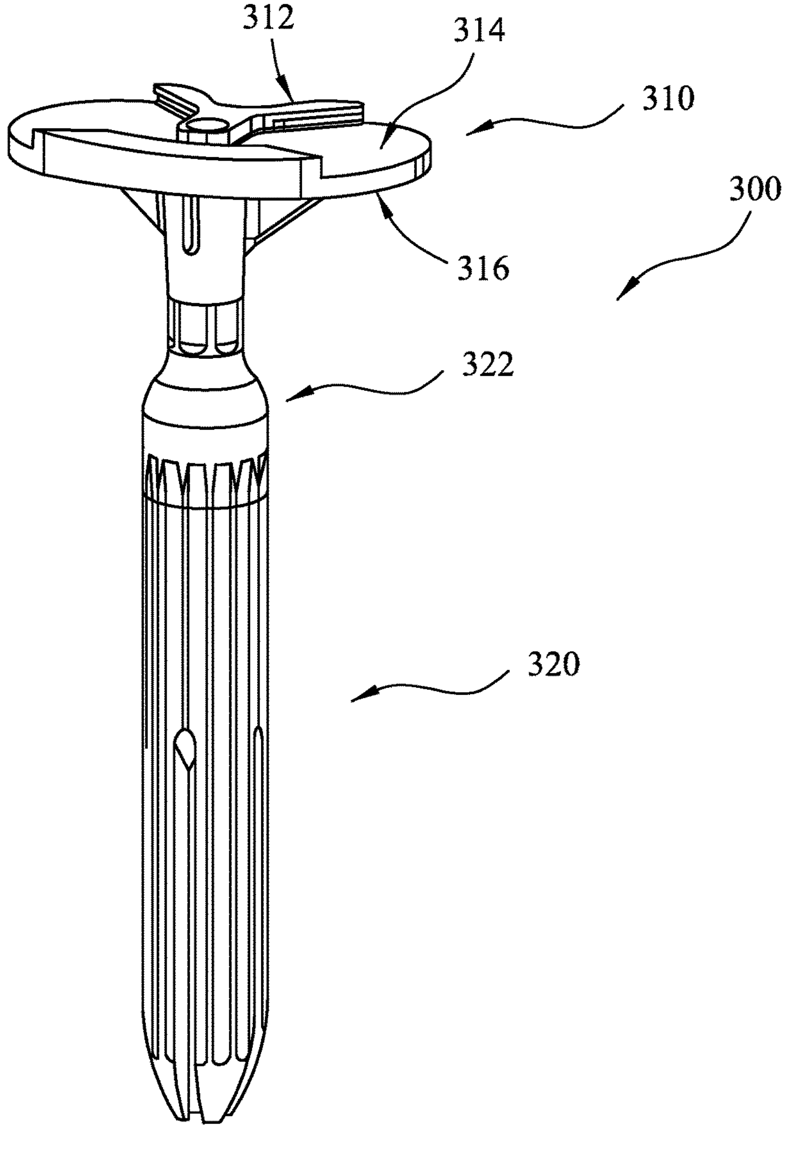
FIG. 7 shows a perspective view from above of a prosthetic implant to which the surgical sensor is releasably attachable.

FIG. 7 shows a perspective view of a prosthetic tibial implant 300. The prosthetic tibial implant 300 includes a prosthetic tibial tray part 310 and a stem part 320 extending from an inferior surface of the tibial tray. As can be seen, the prosthetic tibial tray part 310 has a generally similar form to the trial tibial implant 250, but omits some of the specific features of the trial tibial implant 250. However, the attachment formation 312 has a generally similar construction to that of the attachment formation 268 of the tibial trial. Also, the superior surface 314 of the prosthetic tibial tray is also parallel to the inferior surface 316 of the prosthetic tibial tray. Hence, when the surgical orientation sensor 140 is attached to the prosthetic tibial tray 310 it has the same orientational relationship to the inferior surface 316 as it does for the trial implant 250.

The stem 320 is in the form of a fluted stem of a plurality of self-cutting teeth and is designed for press-fit fixation within a prepared intra-medullary cavity of the tibia of the patient. The self-cutting teeth and press-fit fixation mean that once the stem 320 is introduced into the intra-medullary cavity, the prosthetic tibial implant is substantially prevented from rotating about its longitudinal axis relative to the tibia of the patient. Hence, it is important that the orientation of the prosthetic tibial implant 300 relative to the tibia is correct before the prosthetic tibial implant 300 is progressed into the tibia of the patient.

The stem 320 may be a modular stem provided in a variety of sizes and including a threaded connection toward a superior end 322 by which different length and diameter stems of different sizes may be interchangeably attached to the tibial tray 310.

The prosthetic tibial tray 310 may be made of a suitable bio-compatible metal, such as a cobalt-chrome alloy and the stem 320 may also be made from a suitable bio-compatible material such as a metal, such as a titanium alloy. As noted above, a polymer bearing component may also be attached to the tibial tray 310 to provide an articulating surface against which the condyles of the femoral implant component may articulate in use.

Figure 8:
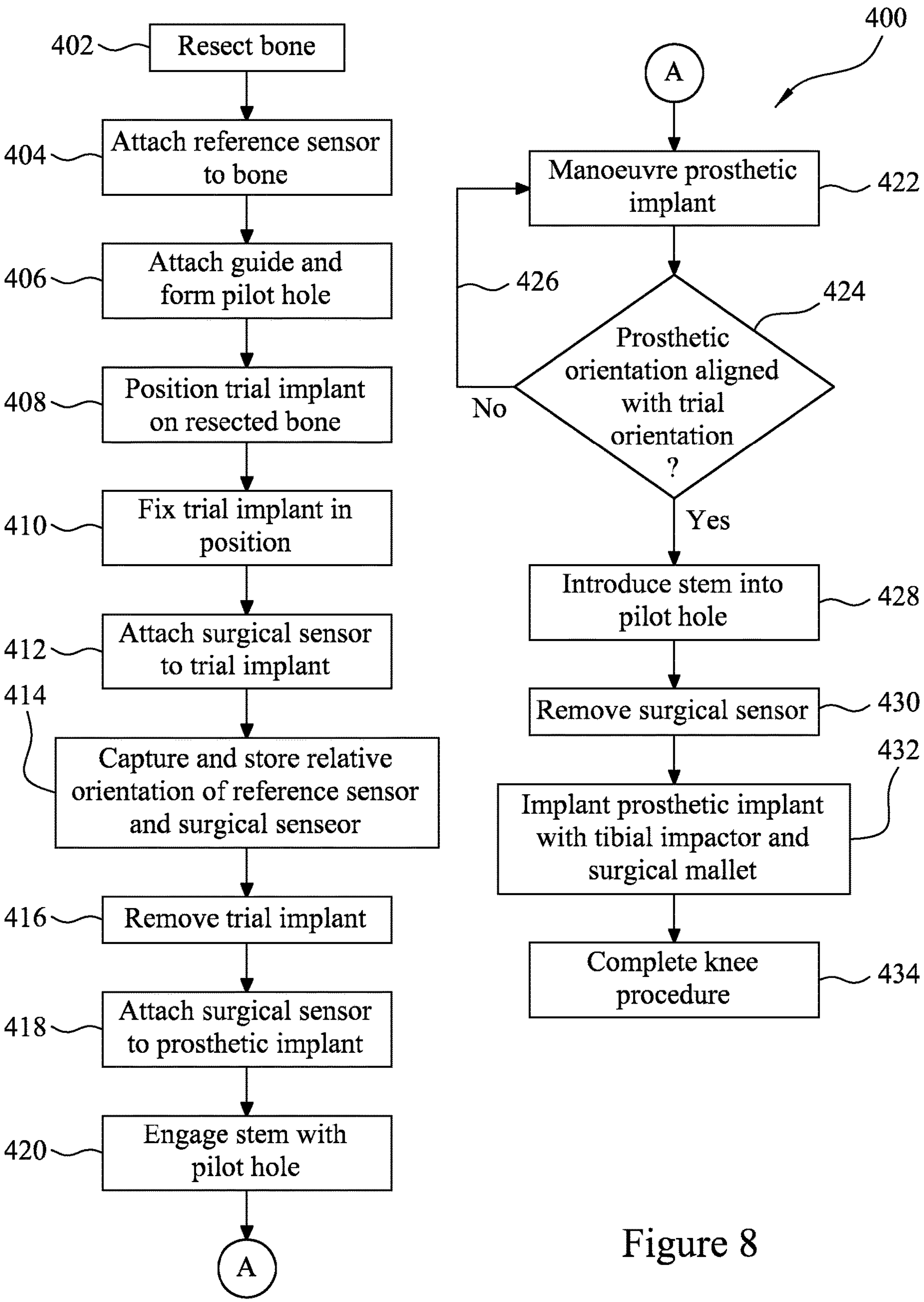
FIG. 8 shows flow chart illustrating a method according to an aspect of the disclosure in which the data processing system of FIG. 1 may be used.

Various methods of use and operation of the apparatus illustrated in FIGS. 1 to 7 will now be described with particular reference to FIGS. 8 and 9. FIG. 8 shows a flow chart illustrating a surgical method which can be carried out using the apparatus and largely done manually by the user, for example, an orthopaedic surgeon.

Figure 9:
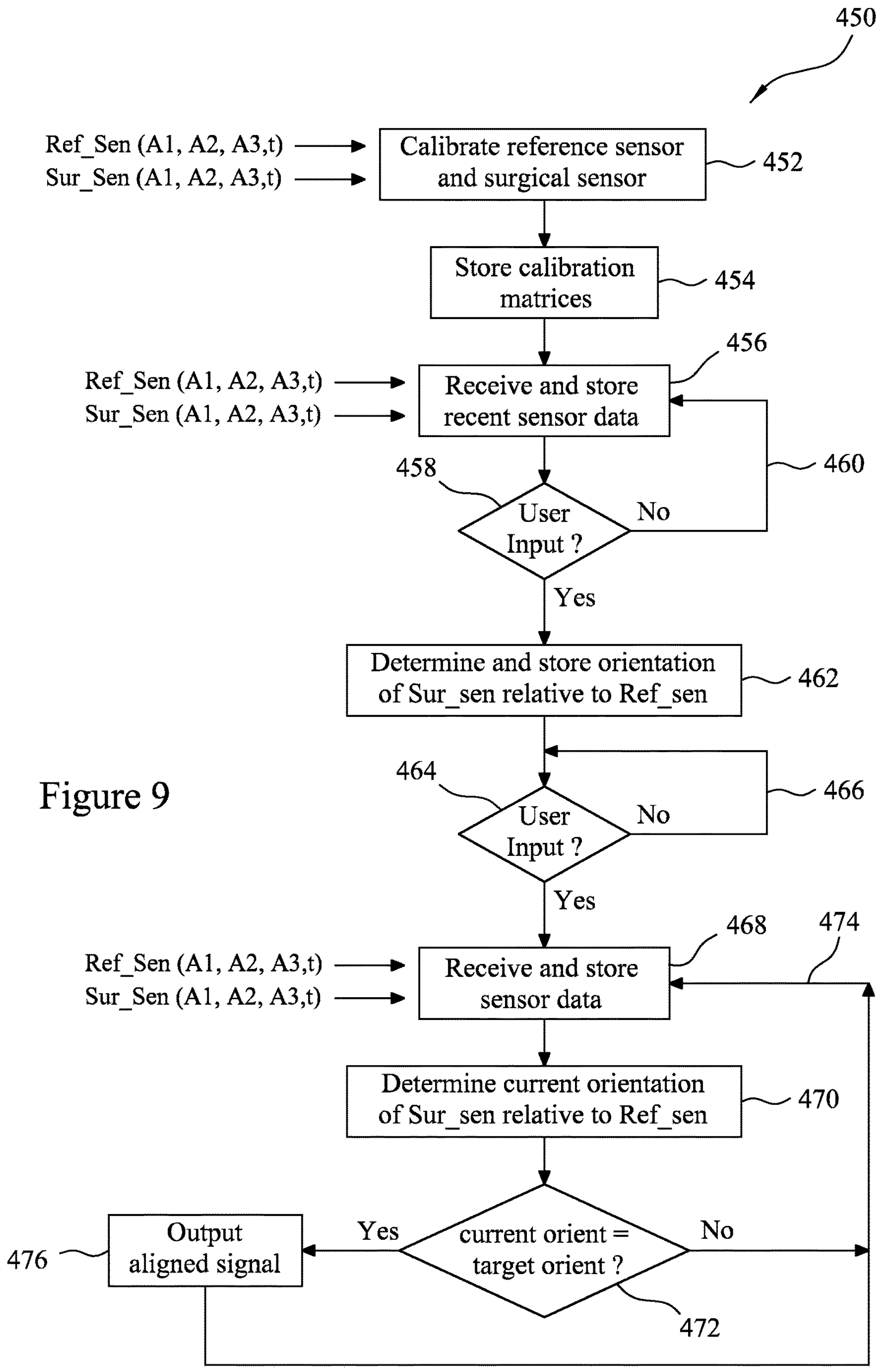
FIG. 9 shows a data processing flow chart according to an aspect of the disclosure and which may be carried out by a data processing apparatus of the data processing system.

FIG. 9 shows a data processing flow chart illustrating a data processing method 450 carried out by the data processing apparatus, e.g. computer 180.

The methods will be described within the context of a total knee replacement surgical procedure and in particular a tibial implant. However, it will be appreciated that the same general method can be applied to other implants of other joints, for example hip joint components and shoulder joint components having stems, and also to surgical instruments in which it is desirable to try to reproduce and initially determine orientation of an implant or instrument.

The surgical method 400 simply illustrates the parts of the surgical procedure relevant for describing the disclosure. It will be appreciated that there are other steps involved which are generally known to a person of ordinary skill in the art and are not described herein in order not to obscure the description of the present disclosure. It will also be appreciated that some of the data processing operations illustrated in FIG. 9 occur in parallel with the surgical method steps illustrated in FIG. 8.

At 402, a proximal tibial cut is made which results in a substantially flat resected tibial bone surface. At 404, the reference orientation sensor 110 is located on the anterior ridge of the tibia and toward the resected portion of the tibia and secured in place by introducing a headed bone pin via aperture 204. As discussed above, the feet 208 are located to the lateral and medial sides of the anterior tibial ridge and therefore help prevent movement of the reference orientation sensor 110 once secured to the patient's tibia.

At 406, a drill guide or similar may be mounted on the resected tibia and used to drill a pilot hole along the tibial axis and substantially perpendicularly to the resected tibial surface. The drill guide may then be removed and any other tibial canal preparation carried out for example using reamers, broaches or similar in order to prepare the tibial intramedullary canal for the press-fit stem.

A handle is attached to the formations 254 in the anterior portion 262 of the tibial tray trial 250 and is used by the surgeon to position the full trial construct, with the stem in the tibial canal, and the tray trail on the resected tibial surface at 408. Once the surgeon is happy with the orientation of the trial implant on the resected tibia, then at 410 first and second bone pins are inserted via bone pin apertures 258, 260 to fix the orientation of the tibial trial on the tibia. At 412, the surgical orientation sensor 140 is attached to the trial tibial implant 250 by engaging lip 226 within the recess defined by the anterior portion 262 and while the surgeon squeezes on the outer limbs 236 of the clip members. Once the under-surface 240 abuts the upper-surface 256 of the tibial trial, then the clip members may be released and will engage in the undercuts 270, 272 of the attachment formation 268.

Previously, the reference orientation sensor and surgical orientation sensor may need to be calibrated relative to each other. The reference orientation sensor may have its own reference frame and the surgical orientation sensor may have its own reference frame. In some embodiments, if those reference frames are not orientationally aligned then it may be necessary to determine the orientational relationship between the reference frames of the orientation sensors in a calibration procedure. If the orientational relationship between the reference frames of the orientation sensors are already known, then that may be stored within the computer system 180. Otherwise, a calibration process may be carried out prior to attaching the reference orientation sensor to the bone and the surgical orientation sensor to the implant.

Referring to FIG. 9, the data processing method 450 may include a calibration process 452. As explained above, the reference orientation sensor generates a time series data stream of three Euler angles (pitch, yaw and roll) and similarly the surgical orientation sensor outputs a time series stream of three Euler angles (pitch, yaw and roll). As generally known in the art, a three by three matrix may be used to implement a rotation about three angular degrees of freedom. Hence, the data processing method generally includes the step of receiving the Euler angle data from the reference orientation sensors and converting the Euler angle data into a corresponding three by three rotation matrix.

At 452, the calibration process may involve determining a rotation matrix for each of the orientation sensors so as to transform the orientation data for each orientation sensor into a common reference frame. For example, the reference orientation sensor and surgical orientation sensor may be held against each other and rotated about 180° to determine a first common axis. They may then be moved between two other orientations through 180° about a rotational axis perpendicular to the first rotational axis. The first and second rotational axis define a plane. The third rotational axis may then be defined as being perpendicular to that plane. Hence, during calibration process 452, angular orientation data is transmitted from the reference as surgical orientation sensors as they are rotated about at least two mutually orthogonal axis and a calibration matrix for the reference orientation sensor and a calibration matrix for the surgical orientation sensor are determined which translate an orientation matrix for the reference orientation sensor and an orientation matrix for the surgical orientation sensor into a common reference frame. The reference sensor calibration matrix and surgical sensor calibration matrix are then each stored at 454.

The reference orientation sensor and surgical orientation sensor each constantly generates and outputs a time series data stream of three angle values when they are powered on. For example, they may output three current angle values a few times per second, for example between 2 to 10 times per second. Hence, as illustrated at 456, the data processing apparatus continuously receives the Euler angle data from each orientation sensor, converts that into respective rotation matrices and stores the rotation matrix data and a time index data value for each of the sensors.

Returning to FIG. 8, at 414, when the surgeon is happy with the position of the trial implant then the orientation of the surgical orientation sensor relative to the reference orientation sensor is captured and stored. It will be appreciated that the tibia may move during the surgical procedure. However, the reference orientation sensor is fixed to the tibia and so does not move relative thereto. Hence, if the orientation of the tibia does change during the surgical procedure, then the corresponding change in the orientation of the reference orientation sensor can be used to compensate for that change in orientation of the tibia.

More specifically, as illustrated in FIG. 9, the data processing apparatus constantly receives and stores recent sensor data. For example, a buffer memory may be used to store the last five seconds worth of sensor data in a FIFO like manner. The most recent five seconds worth of data is retained and older data is discarded as new data is received. If a user input is not detected at 458, then the computer simply continues to receive and store the most recent sensor data at 456. However, once the surgeon is happy with the positioning of the tibial trial implant, then the surgeon may press a button on the computer or a touch screen thereof, to cause the relative orientation of the reference sensor and surgical sensor to be captured and stored. Hence, at 462, a target orientation of the surgical orientation sensor relative to the reference orientation sensor is determined and stored.

More specifically, a current rotation matrix for the surgical sensor is determined and multiplied by the calibration matrix for the surgical orientation sensor to determine a current orientation of the surgical reference sensor in the common frame of reference. Similarly, a current rotation matrix for the reference orientation sensor is determined and multiplied by the reference orientation sensor calibration matrix to determine a current rotation matrix for the reference orientation sensor is determined and multiplied by the reference orientation sensor calibration matrix to determine a current rotation matrix for the reference orientation sensor in the common frame of reference. Then the orientation matrix for the reference orientation sensor in the common frame of reference is multiplied by the rotation matrix for the surgical orientation sensor in the common frame of reference to generate a target orientation matrix which defines the relative orientation of the surgical orientation sensor relative to the reference orientation sensor in the common frame of reference.

Once the orientation of the surgical orientation sensor relative to the reference orientation sensor has been captured and stored at 414, then at 416 the trial implant construct and surgical orientation sensor may be removed by sliding the tibial tray 250 over any the bone pins used to hold the tibial trial in place. The trial implant is removed at 416, and the bone pins may be removed from the resected tibial surface. At some stage, the surgical orientation sensor 140 is removed from the trial implant 250.

Then, at 418, the surgical orientation sensor 140 is attached to the prosthetic implant 300. In particular, as discussed above, and illustrated in FIGS. 6 and 7, the prosthetic tibial tray implant 310 has a generally similar form to the trial tray implant 250. Hence, when surgical orientation sensor 140 is mounted in a similar position on the prosthetic implant 310, then the orientational relationship between the surgical orientation sensor 140 and the prosthetic implant 310 is substantially identical to that between the surgical orientation sensor 140 and the trial implant 250. As also discussed above, a fluted stem 320 with a plurality of cutting teeth extends from the underside of the tibial tray 310.

Once the surgical orientation sensor has been attached to the prosthetic implant at 418, then a distal end of the stem 320 may be introduced into the pilot hole at 420.

As discussed above, the stem includes self-cutting teeth and is designed for press-fit fixation within the intra-medullary canal of the tibia. Hence, it is important to ensure that the orientation along the longitudinal axis of the stem 320 is correct before introducing the stem further into the pilot hole otherwise the tibial tray may be mis-orientated and/or will not sit flush against the resected tibial surface.

Also, the self-cutting teeth prevent rotation of the stem about its longitudinal axis. It is therefore also important that the prosthetic implant 300 is properly aligned to avoid mis-rotation of the tibial tray 310 about the tibial axis.

Hence, the surgical orientation sensor is used to indicate when the orientation of the prosthetic tibial tray 310 is parallel with the previously determined orientation of the trial implant, which is known to have the correct orientation as it was seated flush with the resected tibial surface, and also the correct angular orientation about the stem axis. Hence, when the surgeon is ready to start aligning the prosthetic implant 300 with the intended orientation, then they may press a button on the computer or via a touch screen to provide user input at 464. Absent this user input, the computer simply waits for further user input, as illustrated by process return line 466. Otherwise, when user input is determined at 464, then processing proceeds to 468 at which the computer again receives and stores data from the reference orientation sensor, still attached to the tibia, and the surgical orientation sensor, now attached to the prosthetic tibial tray 310.

At 422, the surgeon may manipulate the prosthetic implant 300, for example by rotating the prosthetic implant about its longitudinal axis to try and generally align the prosthetic implant about its longitudinal rotational axis. The surgeon may also pivot the prosthetic implant 300 to try and generally align its longitudinal axis with the longitudinal axis of the tibia. As the prosthetic implant is manoeuvred by the surgeon at 422, the computer continues to receive and stores sensor data from the reference sensor and surgical sensor. At 470, the current orientation of the surgical sensor relative to the reference sensor is determined.

In particular, a current surgical rotation matrix in a common frame of reference is determined from a current surgical sensor rotation matrix and the surgical sensor calibration matrix. Similarly, a current reference rotation matrix in the common frame of reference is determined from the current reference sensor rotation matrix and the reference sensor calibration matrix. These matrices are multiplied in order to provide a current relative orientation of the surgical orientation sensor relative to the reference orientation sensor in the common frame of reference. At 472, it is determined if the current relative orientation matches the previously determined and stored target orientation matrix as determined previously at 462.

This may be achieved in a number of ways. Ideally, the current relative orientation should match the target relative orientation to within a few degrees, e.g. about 2°. As noted above, a rotation matrix generally includes nine elements. Hence, a first approach would be to determine the differences between the respective nine elements of the current orientation matrix and target orientation matrix and compare the sum of the differences to a threshold value. Additionally, a check may be made whether the difference between any pair of corresponding values in the current orientation matrix and target orientation matrix exceed a further threshold value, for example to indicate that at least one of the angles is too great. Irrespective of the methods used to compare the current relative orientation and target relative orientation if at 472, it is determined that the current orientation does not match the target orientation, then process flow returns as illustrated by process flow line 474 and the computer continues to receive and store sensor data and repeatedly determines the current relative orientations and compares the current relative orientation with the target relative orientation.

If at 472, it is determined that the current orientation does sufficiently match the target relative orientation, then processing proceeds to 476 and a signal is output to indicate that the current orientation does match the target orientation. Hence, for example, the light 224 may change colour, for example from red to green, to signify to the user that the orientation of the prosthetic tibial tray 310 now matches the orientation of the trial tibial tray, as illustrated at 424. Hence, if the surgeon determines at 424 that the light 224 is still red, then they may continue to manoeuvre the prosthetic implant as illustrated by process flow line 426. Otherwise, when the light 224 is green, then the surgeon may determine at 424 that the prosthetic implant now has an orientation matching the orientation of the trial implant. It will be appreciated that it is not the positions of the trial implant and prosthetic implant that match as the prosthetic tibial tray 310 is translated away from the resected plane of the tibia compared to the position of the trial tibial tray 250. However, as the orientation of the prosthetic tibial tray 310 now substantially matches the orientation of the trial tibial tray 250, and which was seated on the resected tibial surface, then the surgeon may be more confident that at the stem is progressed into the pilot hole, then the prosthetic tibial tray will also adopt the same orientation relative to the tibia as the trial tray did.

Hence, at 428, the surgeon may progress the stem 320 into the pilot hole confident that the orientation of the prosthetic implant is substantially correct. As noted above, the stem 320 is self-cutting for press-fit fixation and therefore once the stem is progressed into the tibia its orientation is largely fixed. After the stem 320 has been progressed into the pilot hole by the surgeon at 428, then the surgeon may remove the surgical orientation sensor 140 at 430. At 432, the surgeon may use a tibial impactor tool and a surgical mallet to further progress the stem 320 into the tibia until the prosthetic tibial tray 310 is sufficiently seated on the resected tibial surface.

After that, the knee surgery procedure may proceed 434 generally conventionally. At some stage, the reference sensor attached to the tibia is removed.

Figure 10:
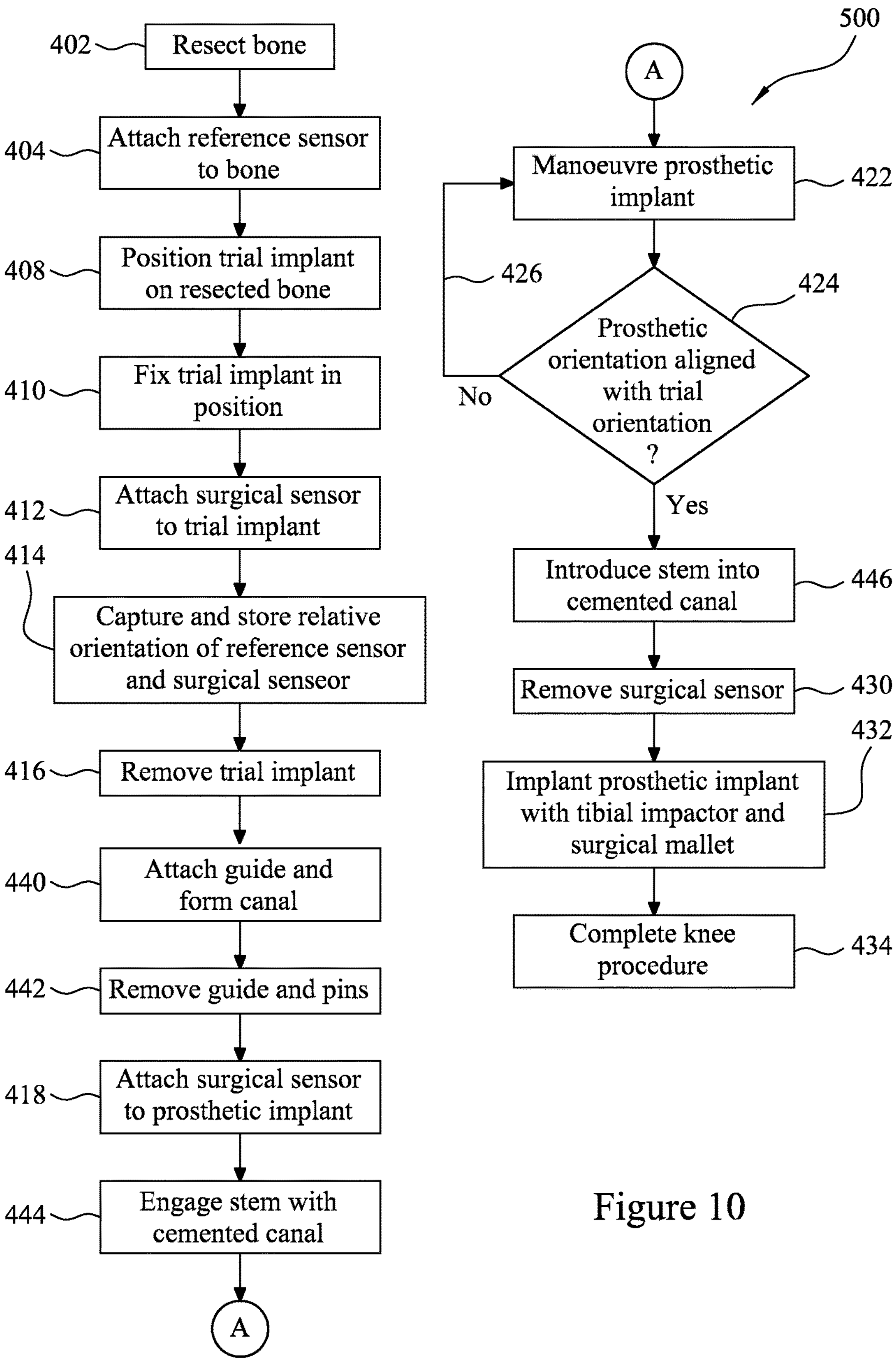
FIG. 10 shows a flow chart illustrating a further method according to an aspect of the disclosure in which the data processing system of FIG. 1 may be used.

FIG. 10 shows a flow chart illustrating a second method 500 similar to the first method 400 illustrated in FIG. 8. Many of the method steps of the second method 500 are similar to those of the first method and hence are numbered in the same way. Also the data processing operations carried out in parallel are generally the same as, or may involve minor modifications to, those illustrated in FIG. 9. The second method 500 illustrated in FIG. 10 may be more suitable for a shorter stem which is cemented in place as the shorter stem does not tend to engage the walls defining the intramedullary canal. Hence, the tibial tray stem tends not to define the rotation of the tibial tray. Rather the location of the tibial tray on the resected proximal tibia is the greater factor in determining the eventual tray orientation. Hence, in the second method 500, the tray orientation may be defined first and before the steps relating to intramedullary canal preparation.

As illustrated in FIG. 10, method 500 begins at 402 by resecting the proximal part of the tibia and then attaching the reference sensor to the tibia at 404. The tibial trail is then placed on the resected tibia and positioned at 408 and then pinned in position at 410. The surgical sensor is then attached to the tibial trial at 412 and the relative orientation of the reference sensor and surgical sensor captured and stored at 414. The trial may then be removed at 416 and the surgical sensor may be removed. A drill guide may then be attached to the resected tibia at 440 using the same bone pins as were used to pin the tibial trial in place at 410. The drill guide may then be used at 440 to start preparation of the tibial intramedullary canal before being removed at 442 and the bone pins removed also. Any further preparation of the tibial intramedullary canal to receive the short tibial stem may then be carried out as required.

The intramedullary canal may then be cemented to fix the tibial stem when inserted therein.

At 418, the surgical sensor may be attached to the prosthetic tibial implant and then the prosthetic stem may be introduced into the intramedullary canal at 444. The prosthetic implant may then be manipulated at 422 by rotating the tibial tray about the stem axis and/or pivoting the stem relative to the intramedullary canal axis until the orientation of the prosthetic tray is determined 424 to match the orientation of the trial tray. The surgeon may then introduce the stem further into the intramedullary canal at 446. The surgical sensor may then be removed at 430 before the prosthetic stem and tray are finally seated at 432 potentially using an impactor and mallet. The remainder of the procedure may then be completed in the usual manner at 434.

Hence, using the reference orientation sensor and surgical orientation sensor to determine a target relative orientation and then using the same surgical orientation sensor attached to a further piece of surgical equipment required to have the same relative orientation, and the surgeon can be more confident that the subsequently used piece of surgical equipment will adopt the same orientation relative to the bone as the initially used piece of surgical equipment.

As noted above, the disclosure is not necessarily limited to tibial trials and tibial prosthetic implants. It may also be applied to other orthopaedic implants. Further, the disclosure is also not limited to implants. The disclosure may also be applied to surgical instruments and tools in which it is desirable to be able to compare a subsequent orientation of the instrument or tool relative to the patient's bone with a previous position of the instrument or tool.

For further example, the reference sensor could be attached to the patient's femur. The surgical sensor could then initially be attached to a femoral rasp or femoral broach or reamer being used to prepare an intramedullary canal within a femur. Or the surgical sensor could be attached to trial femoral stem, for example to its neck, and the trial stem located in a prepared femoral intramedullary cavity. The surgical sensor could then subsequently be attached to a prosthetic stem, for example to its neck, in order to ensure that the prosthetic stem has the same orientation relative to the patent's femur as the instrument used to prepare the femoral cavity or the trial stem within the femoral intramedullary cavity. This may be particularly beneficial when a cementable prosthetic stem is used as that often has a smaller size than the corresponding trial stem in order to accommodate a cement mantel within the femur and hence there can be scope for significant variation in the orientation of the prosthetic stem relative to the femur within the femoral intramedullary cavity when the prosthetic stem is introduced into the cement within the intramedullary cavity and while the cement is setting.

Figure 11:
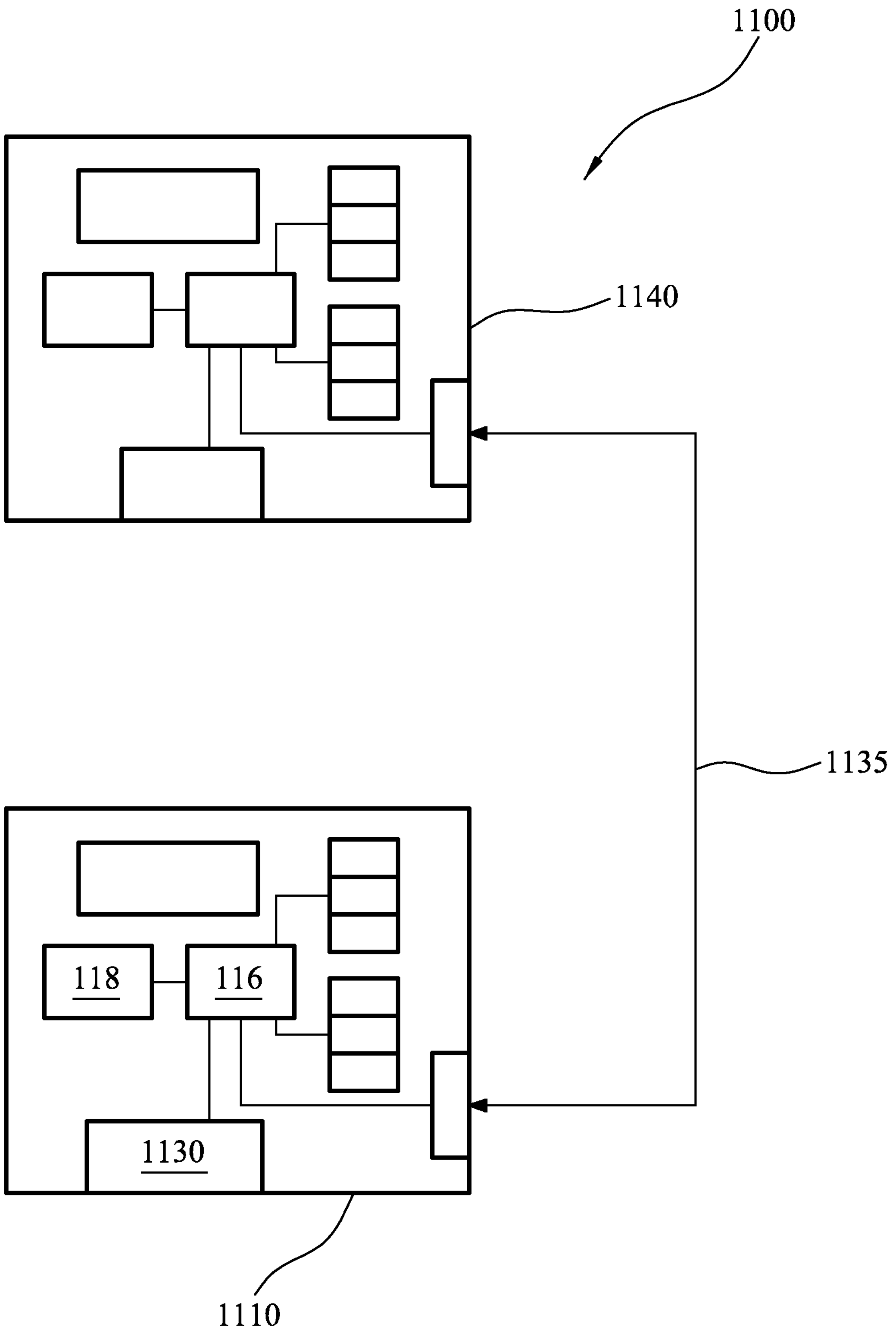
FIG. 11 shows a schematic block diagram of a second embodiment of a data processing system according to an aspect of the disclosure.

FIG. 11 shows a second embodiment 1100 of a data processing system similar to that shown in FIG. 1. The data processing system 1100 again includes a reference orientation sensor 1110 and a surgical orientation sensor 1140. However, in this embodiment, the data processing functions provided by the general purpose computer 180 in FIG. 1 are instead provided by the reference orientation sensor 1110. It will be appreciated that the reference orientation sensor 1110 may have the greater size than the surgical orientation sensor 1140 and therefore may be easier to accommodate the extra computational resources that may be required. Hence, the reference orientation sensor also includes a user input/output interface 1130, for example in the form of physical buttons and/or a touch screen, via which the surgeon may interact with the system, in place of the computer 180 of FIG. 1. Also, as illustrated by communication link 1135, a two way communication link is provided between the reference orientation sensor 1110 and the surgical orientation sensor 1140, for example using Bluetooth of Wi-Fi to provide a wireless connection or via a USB connection to provide a wired communication route. Hence, the reference orientation sensor 1110 may send command and/or control instructions to the surgical rotation sensor and/or receive time series angle data from the surgical orientation sensor. Hence, the data processing operations illustrated in FIG. 9 are largely carried out by the processor 116 of the reference orientation sensor as a control suitable data processor executable instructions stored in on-board memory 118.

In this specification, example embodiments have been presented in terms of a selected set of details. However, a person of ordinary skill in the art would understand that many other example embodiments may be practiced which include a different selected set of these details. It is intended that the following claims cover all possible example embodiments.

Any instructions and/or flowchart steps can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are covered as well.

The invention claimed is:

1. A surgical system, comprising:

a reference orientation sensor operable to generate an electronic signal indicative of a reference orientation and having a first attachment feature by which the reference orientation sensor is attachable to a limb of a patient in use;

a prosthetic implant configured to be implanted on a patient's limb, the prosthetic implant including a number of undercuts formed on a proximal side;

an implant trial configured to be coupled to the patient's limb during surgery, the implant trial including a number of undercuts formed on a proximal side and a surface that corresponds to a surface of the prosthetic implant;

a surgical equipment orientation sensor operable to generate an electronic signal indicative of a surgical equipment orientation when attached to one of the prosthetic implant and the implant trial, the surgical equipment orientation sensor having a pair of mutually opposed spring-loaded members arranged to separately engage with the undercuts of one of the prosthetic implant and implant trial to secure the surgical equipment orientation sensor in a corresponding position on each of the prosthetic implant and implant trial; and a data processing apparatus, the data processing apparatus including a data processor and a storage device storing non-transitory instructions executable by the data processor to:

receive an electronic signal indicating a first reference orientation from the reference orientation sensor indicative of an initial orientation of the patient's limb, receive an electronic signal indicating a first surgical equipment orientation from the surgical equipment orientation sensor indicative of an orientation of the implant trial when the implant trial is coupled to the surgical equipment orientation sensor, determine and electronically store an initial relative orientation based on the first reference orientation and the first surgical equipment orientation, receive an electronic signal indicating a second reference orientation from the reference orientation sensor indicative of a current orientation of the patient's limb, receive an electronic signal indicating a second surgical equipment orientation from the surgical equipment orientation sensor indicative of an orientation of the prosthetic implant when the prosthetic implant is coupled to the surgical equipment orientation sensor, determine and electronically store a current relative orientation based on the second reference orientation and the second surgical equipment orientation, and generate an output signal when the current relative orientation matches the reference relative orientation indicating that the prosthetic implant currently has the same orientation on the patient's limb as the implant trial component as when the initial relative orientation was determined, the output signal being at least one of a visual and audible output signal.

2. The surgical system as claimed in claim 1, wherein the surgical equipment orientation sensor includes an output device arranged to receive the output signal and to change state when the output signal is received.

3. The surgical system as claimed in claim 2, wherein the output device is a visual output device.

4. The surgical system as claimed in claim 1, wherein the data processing apparatus is included in the surgical equipment orientation sensor or the reference orientation sensor.

5. The surgical system as claimed in claim 1, wherein the data processing apparatus is a separate device to the surgical equipment orientation sensor and the reference orientation sensor, and wherein and the reference orientation sensor includes a first communication interface via which the reference orientation sensor can transmit to the data processing apparatus and the surgical equipment orientation sensor includes a second communication interface via which the surgical equipment orientation senor can communicate with the data processing apparatus.

6. The surgical system as claimed in claim 1, wherein the prosthetic implant includes an elongate member configured to be received in a cavity defined by a bone of a patient and wherein the elongate member includes at least one formation configured to interact with bone to inhibit rotation of the elongate member relative to the bone.

7. The surgical system as claimed in claim 6, wherein the elongate member is a stem and the at least one formation is a self-cutting tooth.

8. The surgical system as claimed in claim 1, wherein the reference orientation sensor includes a support formation configured to interact with a bony anatomical feature of the limb of the patient and to resist movement of the reference orientation sensor relative to the limb of the patient.

9. The surgical system as claimed in claim 1, wherein the orthopaedic implant is a tibial tray.

10. The surgical system as claimed in claim 1, wherein the limb is a tibia.

11. The surgical system as claimed in claim 1, and further comprising:

a surgical instrument having an instrument attachment feature to which the surgical equipment orientation sensor is releasably attachable.

12. The surgical system as claimed in claim 1, and further comprising:

a surgical instrument or an implant, the surgical instrument or implant having an attachment feature to which the surgical equipment orientation sensor is releasably attachable and also having a bone modifying feature configured to modify a bone in use.

13. The surgical system as claimed in claim 1, wherein the reference orientation sensor comprises an inertial measurement unit and the surgical equipment orientation sensor comprises an inertial measurement unit.

* * * * *